(12) United States Patent
Hugger et al.

(10) Patent No.: US 11,717,704 B2
(45) Date of Patent: Aug. 8, 2023

(54) INTERVENTIONAL PEAK SKIN DOSE (PSD) ESTIMATION

(71) Applicant: KONINKLIJKE PHILIPS N.V., Eindhoven (NL)

(72) Inventors: Norbert Hugger, Andover, MA (US); Andrew Daudelin, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 336 days.

(21) Appl. No.: 17/092,232

(22) Filed: Nov. 7, 2020

(65) Prior Publication Data

US 2021/0138271 A1 May 13, 2021

Related U.S. Application Data

(60) Provisional application No. 62/932,527, filed on Nov. 8, 2019.

(51) Int. Cl.
*A61N 5/10* (2006.01)
*A61B 6/00* (2006.01)

(52) U.S. Cl.
CPC .......... *A61N 5/1065* (2013.01); *A61B 6/5217* (2013.01); *A61B 6/542* (2013.01); *A61N 5/1049* (2013.01); *A61N 2005/1059* (2013.01)

(58) Field of Classification Search
CPC ............... A61N 5/1065; A61N 5/1049; A61N 2005/1059; A61B 6/5217; A61B 6/542
See application file for complete search history.

(56) References Cited

U.S. PATENT DOCUMENTS

| | | | |
|---|---|---|---|
| 2009/0161827 A1* | 6/2009 | Gertner | A61N 5/1017 378/65 |
| 2015/0071407 A1 | 3/2015 | Watanabe et al. | |
| 2015/0224343 A1 | 8/2015 | Couture et al. | |
| 2017/0007196 A1* | 1/2017 | Don | A61B 6/4417 |

OTHER PUBLICATIONS

Khodadadegan, et al., Validation and Initial Clinical Use of Automatic Peak Skin Dose Localization with Flouroscopic 246-255.
Johnson, et al., "Skin dose mapping for flouroscopically guided inverventions", Med. Phys. 38 (10), Oct. 2011, pp. 5490-5499.

\* cited by examiner

*Primary Examiner* — David P Porta
*Assistant Examiner* — Fani Polyzos Boosalis

(57) ABSTRACT

An apparatus comprises at least one electronic processor programmed to: control an imaging device to perform an imaging procedure on a patient wherein the imaging procedure comprises a plurality of radiation exposure events; automatically construct a data structure which stores information for the radiation exposure events including at least radiation dose information for the radiation exposure events determined during the imaging procedure; compute a peak skin dose (PSD) estimate for the imaging procedure from the information for the radiation exposure events retrieved from the data structure; determine whether the PSD estimate exceeds a PSD threshold; and output a notification if the PSD estimate exceeds the PSD threshold.

20 Claims, 4 Drawing Sheets

INTERVENTIONAL PEAK SKIN DOSE (PSD) ESTIMATION

RELATED APPLICATION

This application claims the benefit of and priority to Provisional Application No. 62/932,527, filed Nov. 8, 2019. These applications are hereby incorporated by reference herein, for all purposes.

FIELD

The following relates generally to the imaging arts, x-ray imaging arts, fluoroscopy imaging arts, radiation safety arts, dosimetry arts, fluoroscopy dose calculation arts, and related arts.

BACKGROUND

X-ray imaging procedures, such as fluoroscopy, can be commonly performed using an apparatus, such as a C-arm, which has an x-ray tube mounted on one arm end and a digital radiation detector mounted on the other arm end. The detector faces the x-ray tube so as to detect the x-ray beam after projection through a patient (or other imaging subject). The C-arm can be moved to image the patient at a number of different angles (sometimes called views) around the imaging subject. At each view, there is a fluoroscopy period and/or an acquisition period. During the fluoroscopy period the digital radiation detector operates in a live mode to provide the operator with a type of preview image. During the acquisition period, an image or a cinematic sequence of images (i.e. a CINE sequence) is acquired, which is the clinical image or CINE sequence that serves as the clinical image for use in diagnosis or other clinical analysis. To reduce total radiation exposure, in some approaches the x-ray tube intensity is lowered during the fluoroscopy period. Nonetheless, depending on the type of fluoroscopic imaging procedure being performed, the total duration of the fluoroscopy period can be longer than the total duration of the acquisition period, which can lead to a higher radiation dose being delivered during the fluoroscopy period than during the acquisition period.

The radiation attenuates as it passes through the patient; hence, the highest radiation dose is delivered to the portion of the patient's skin at which the x-ray beam is incident. During fluoroscopic imaging (for example, during a fluoroscopically guided interventional procedure using a C-arm fluoroscope), there is the potential for excessive x-ray dose to the skin leading to formation of necrotic skin lesions. The peak skin dose (PSD) is a metric for estimating likelihood of such skin damage. However, estimating the PSD usually requires a user to manually input information about the fluoroscopic imaging procedure, and the PSD estimate is computationally complex, and commonly relies upon estimated parameter values based on the nominal (i.e., expected or scheduled) imaging procedure. These estimated parameter values may be inaccurate if the actual imaging procedure deviates from the expected nominal procedure. For example, if the operator has some difficulty obtaining a particular view, this may increase the duration of the fluoroscopy period resulting in higher skin dose for that view; or, if the x-ray tube output is different from the expected output this can introduce error in the PSD estimate.

The following discloses certain improvements to overcome these problems and others.

SUMMARY

In one aspect, an apparatus comprises at least one electronic processor programmed to: control an X-ray imaging device to perform an X-ray imaging procedure on a patient wherein the X-ray imaging procedure comprises a plurality of radiation exposure events; automatically construct a data structure which stores information for the radiation exposure events including at least radiation dose information for the radiation exposure events determined during the X-ray imaging procedure; compute a PSD estimate for the X-ray imaging procedure from the information for the radiation exposure events retrieved from the data structure; determine whether the PSD estimate exceeds a PSD threshold; and output a notification if the PSD estimate exceeds the PSD threshold.

In another aspect, a non-transitory computer readable medium stores instructions executable by at least one electronic processor to perform a PSD computation method that includes: controlling an imaging device to perform an imaging procedure on a patient wherein the imaging procedure comprises a plurality of radiation exposure events; estimating a per-point skin dose value for points on a skin model representing the patient from information for the radiation exposure events, the skin model comprising a flattened ellipsoid calculated from polar coordinates from a center of the flattened ellipsoid and a radius of a shape along each of a corresponding x-axis, y-axis, and z-axis of the flattened ellipsoid; and computing a PSD estimate as the largest per-point skin dose value.

In another aspect, a PSD computation method includes: controlling a fluoroscope to perform a fluoroscopy procedure on a patient wherein the fluoroscopy procedure comprises a plurality of radiation exposure events; automatically constructing a data structure which stores information for the radiation exposure events including at least radiation dose information for the radiation exposure events determined during the fluoroscopy procedure; estimating a per-point skin dose value for points on a skin model representing the patient from the information for the radiation exposure events retrieved from the data structure; determining a three-dimensional position for the skin model using table coordinates retrieved from the data structure by operations including: retrieving a table height value, a table thickness value, and a pad thickness value from the data structure; and adjusting the table height value for the table thickness value and the pad thickness value to determine a height for the skin model; and computing the PSD estimate as the largest per-point skin dose value based on the three-dimensional position for the skin model.

One advantage resides in automatically calculating a PSD value for a patient immediately after an X-ray procedure.

Another advantage resides in notifying a patient to seek medical treatment if a calculated PSD value is too high.

Another advantage resides in using a flattened ellipsoid model to calculate a PSD value.

Another advantage resides in determine exit points on a patient as points which a ray passes inside the flattened ellipsoid model to calculate a PSD value.

Another advantage resides in calculating the PSD value immediately after an X-ray procedure, such as a fluoroscopy procedure, using the automatically generated Radiation Dose Structured Report (RDSR) or other automatically generated data structure which records radiation exposure information for the completed fluoroscopy procedure.

Another advantage resides in using thickness values of a table and pad on which the patient lies during an X-ray procedure, such as a fluoroscopy procedure, to calculate a PSD value.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
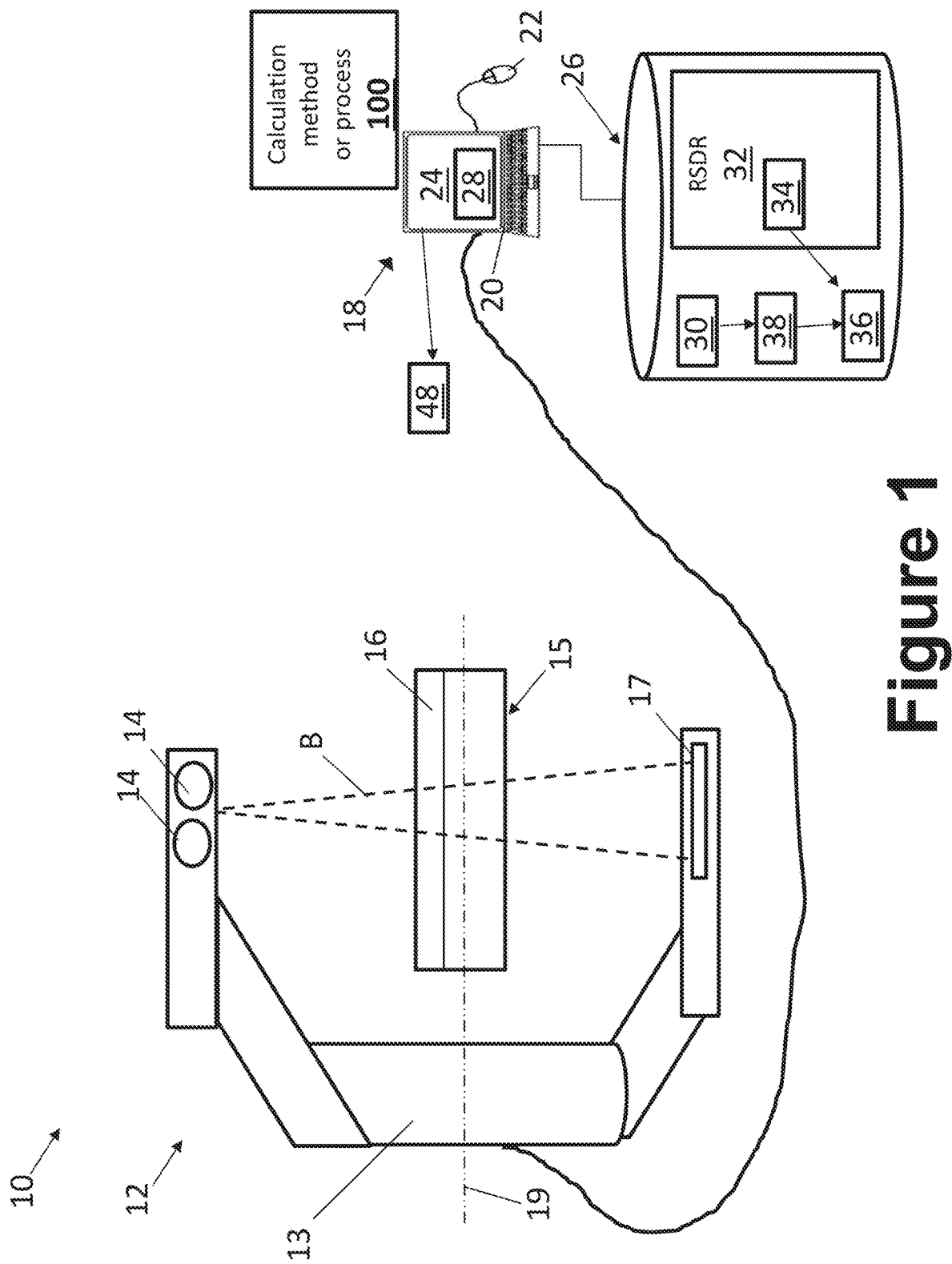
FIG. 1 diagrammatically illustrates an illustrative apparatus for computing a PSD estimate in accordance with the present disclosure.

The following discloses leveraging information contained in a Radiation Dose Structured Report (RDSR) or other Digital Imaging and Communication in Medicine (DICOM) data structure automatically created to document an X-ray procedure (for example, a fluoroscopy procedure) in order to automatically compute a PSD estimate without requiring additional user input beyond the content of the RDSR. In this way, immediately upon completion of the fluoroscopic procedure the PSD estimate is calculated, and if it is above a threshold then a notification is automatically issued, for example indicating that the PSD during the procedure was high and suggesting follow-up with the patient's physician or a dermatologist. The skin dose calculation is performed for each point on the skin model on a "per event" basis, where each event is a radiation exposure event, and with modeling of the directionality of the x-ray beam, and the total dose to each point on the skin model is then accumulated over the events. As used herein, the term "radiation exposure event" (and variants thereof) refer to a time interval in which the patient undergoing the fluoroscopy imaging procedure is exposed to x-ray radiation.

To enable estimation of the PSD immediately after completion of a fluoroscopy procedure, a computationally efficient PSD estimation should be used. The computational efficiency of the PSD estimation depends, in part, on the complexity of the modeling of the skin. In some aspects disclosed herein, an improved skin model is used in the PSD calculation. Some existing approaches employ an ellipsoid, or a set of ellipsoids. A single ellipsoid is a very rough estimate of the patient's skin; while, a set of ellipsoids substantially increases the computational complexity of the PSD calculation. The disclosed approach employs a single flattened ellipsoid that better approximates the flatness of the patient's back and front sides, while retaining the computational efficiency of using a single closed geometrical surface that is continuous and fully differentiable everywhere.

In other aspects disclosed herein, the patient table and the pad used in the fluoroscopy procedure are accounted for in the PSD calculation. The latter can substantially impact the z-directional coordinates of the patient, as the pad can be thicker than the table, and also introduces some x-ray attenuation when the beam is underneath the table.

In further aspects disclosed herein, certain points on the skin of the patient are efficiently determined to be exit points based on the geometrical analysis that the ray passing from the source to the point on the skin passes inside the flattened ellipsoid skin model.

In yet other aspects disclosed herein, in order to provide the automatic PSD calculation, the disclosed system defines default values for certain values that may not be available in the RDSR or other DICOM data structure documenting the fluoroscopic procedure. This facilitates using the PSD calculator for older systems that may provide less complete RSDR documentation. It will be appreciated that the various aspects mentioned above are not mutually exclusive. A specific implementation may include only a single one of the above aspects, or may include some subset of the above aspects, or may include all of the above aspects.

While primarily described in terms of fluoroscopy procedures, it will be appreciated that the disclosed systems and methods can be used in conjunction with any suitable X-ray imaging procedure, such as C-arm interventional imaging.

With reference to FIG. 1, an apparatus 10 for calculating a PSD dose value is shown. As shown in FIG. 1, the apparatus 10 includes or is operatively connected to an X-ray imaging device, such as a fluoroscope 12 (e.g., an illustrated C-arm fluoroscope) comprising typical components, such as one or more x-ray sources 14 (e.g., an x-ray tube 14) disposed at one distal end of a C-arm 13, a table 15 disposed at a proximal end of the C-arm, and a pad 16 disposed on top of the table and on which a patient lies on for a fluoroscopic procedure. A digital radiation detector 17 is disposed at the other distal end of the C-arm 13, in the path of a radiation beam B emitted by the x-ray source(s) 14, to detect radiation projected by the x-ray source 14 after passing through (and being attenuated by) the pad 16 and table 15 and a patient (not shown) disposed on the pad 16. The C-arm 13 is rotatable about an axis 19 by way of a robotic mount (not shown) to position the x-ray source 14 and opposite detector 17 at a desired angle (or view). The robotic mount may provide additional degrees of mechanical freedom to achieve a desired view. By way of nonlimiting illustrative example, the fluoroscope 12 may be a Philips Allura Xper fluoroscope (available from Koninklijke Philips N.V.) At each view, the x-ray source 14 and radiation detector 17 may be operated in fluoroscopy mode to provide the fluoroscope operator with a live preview image, thereby allowing the operator to confirm the desired view has been obtained. Thereafter, the fluoroscope is operated in an imaging mode to acquire to an image, or a cinematic sequence of images (i.e. CINE sequence). Each such view is treated herein as a radiation exposure event (sometimes referred to as an "event" for brevity). In general, each radiation exposure event may include a fluoroscopy time and an acquisition time. In the illustrative examples, the radiation doses are quantified herein using air kerma (AK) units. Hence, for each radiation exposure event there may be a fluoroscopy AK which is the radiation dose delivered during the fluoroscopy time, and an acquisition AK which is the radiation dose delivered during the acquisition time.

As diagrammatically shown in FIG. 1, the apparatus 10 also includes a workstation 18, such as an electronic processing device, a workstation computer, or more generally a computer. Additionally or alternatively, the remote workstation 18 can be embodied as a server computer or a plurality of server computers, e.g. interconnected to form a server cluster, cloud computing resource, or so forth. The workstation 18 includes typical components, such as an electronic processor 20 (e.g., a microprocessor), at least one user input device (e.g., a mouse, a keyboard, a trackball, and/or the like) 22, and at least one display device 24 (e.g. an LCD display, plasma display, cathode ray tube display, and/or so forth). In some embodiments, the display device 24 can be a separate component from the workstation 12. The display device 24 may also comprise two or more display devices, The electronic processor 20 is operatively connected with a one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the workstation 12, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors. The non-transitory storage media 26 stores instructions executable by the at least one electronic processor 20. The instructions include instructions to generate a graphical user interface (GUI) 28 for display on the remote operator display device 24.

The workstation 12 is configured as described above to perform a PSD computation method or process 100. The non-transitory storage medium 26 stores instructions which are readable and executable by the at least one electronic processor 20 of the workstation 12 to perform disclosed operations including performing the method or process 100. In some examples, the method 100 may be performed at least in part by cloud processing.

Figure 2:
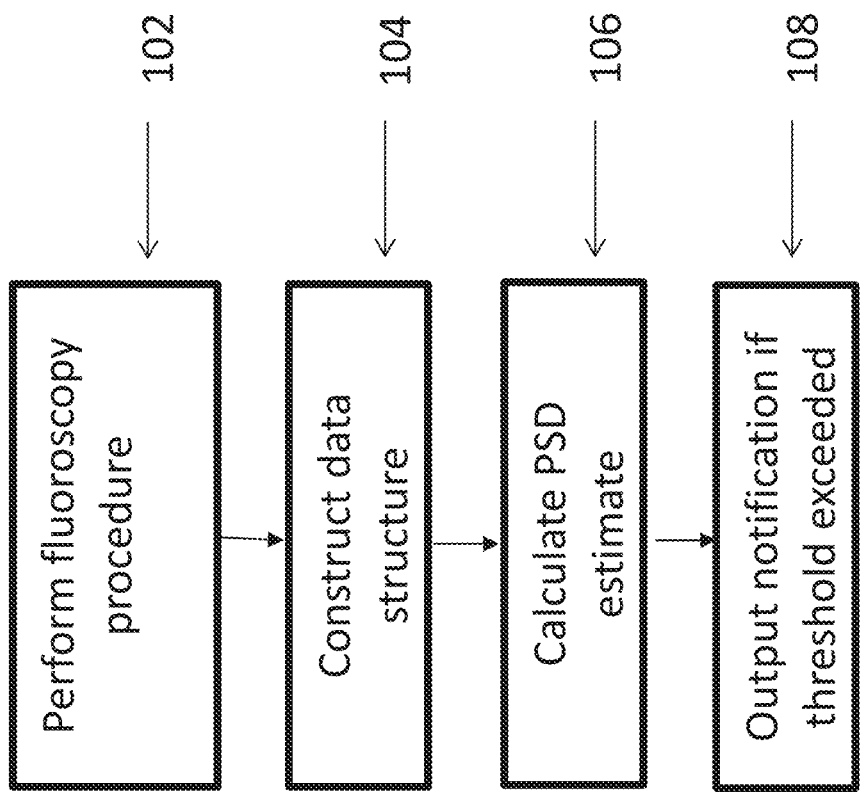
FIG. 2 shows example flow chart operations performed by the apparatus of FIG. 1.

Referring now to FIG. 2, and with continuing reference to FIG. 1, an illustrative embodiment of the method or process 100 is diagrammatically shown as a flowchart. At an operation 102, the at least one electronic processor 20 is programmed to control the fluoroscope 12 to perform a fluoroscopy procedure on a patient. The fluoroscopy procedure includes a plurality of radiation exposure events 30.

In some embodiments, at an operation 104, the at least one electronic processor 20 is programmed to automatically construct a data structure 32. In some examples, the data structure 32 can comprise a standard data structure containing information related to the X-ray imaging procedure, such as a DICOM data structure, and in more specific examples, the data structure comprises a RDSR (which includes information such as dose templates, image headers, dose reporting, and so forth), and can be stored in the non-transitory computer readable medium 26. The data structure 32 stores information 34 for the radiation exposure events 30. The information 34 can include, for example, radiation dose information for the radiation exposure events 30 determined during the fluoroscopy procedure. In other examples, the radiation dose information 34 can be determined based on one or more settings of the fluoroscope 12 during the radiation exposure events 30, along with fluoroscopy times and acquisition times of the events. The RDSR or other DICOM data structure 32 is generated after completion of the fluoroscopy procedure (some portions may be generated during the fluoroscopy procedure) so as to store actual information such as fluoroscopy AK and acquisition AK values measured directly or indirectly (e.g., based on monitored x-ray tube operating parameters) for each event, and may be stored in a Picture Archiving and Communications System (PACS) (not shown) and/or a Radiology Information System (RIS) (not shown) along with the acquired fluoroscope images.

Figure 3:
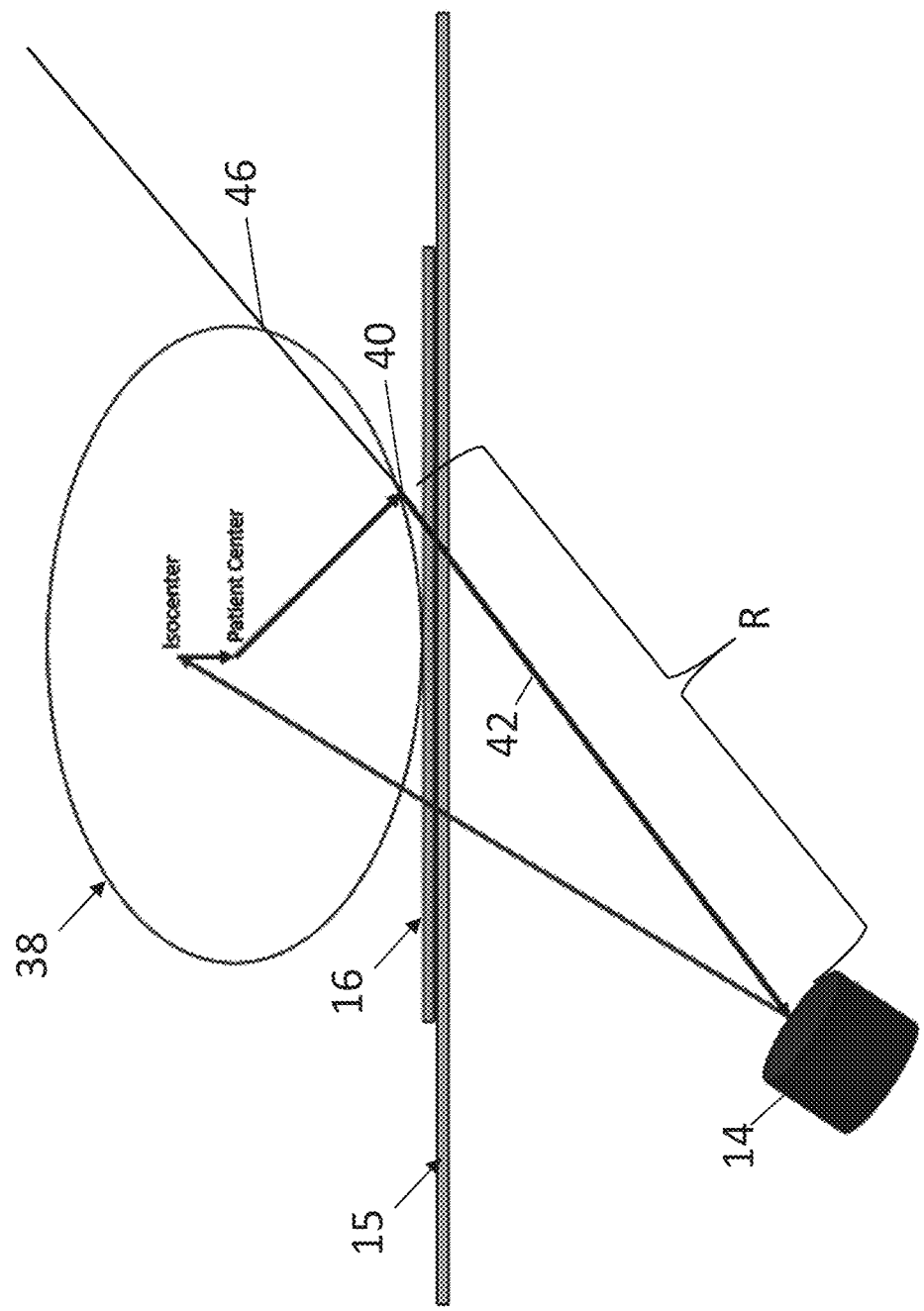
FIG. 3 shows an example of a skin model used by the apparatus of FIG. 1.

With continuing reference to FIGS. 1 and 2, and now referring to FIG. 3, at an operation 106, the at least one electronic processor 20 is programmed to compute a PSD estimate 36 for the fluoroscopy procedure from the information 34 for the events 30 retrieved from the data structure 32. In one example, the PSD estimate 36 is computed using only the information 34 in the data structure 32. In another example, the PSD estimate 36 is computed using default parameter values stored in the non-transitory computer readable medium 26.

In some embodiments, the PSD estimate 36 can be computed by estimating a per-point skin dose value for corresponding points 40 on a skin model 38 representing the patient from the information 34 for the radiation exposure events 30 retrieved from the data structure 32. The dose value 40 having the highest value is the PSD estimate 36.

In one example embodiment, as shown in FIG. 3, the skin model 38 comprises a flattened ellipsoid calculated from polar coordinates from a center of the flattened ellipsoid and a radius of a shape along each of a corresponding x-axis, y-axis, and z-axis of the flattened ellipsoid. In this embodiment, the per-point skin dose value for each point 40 on the skin model 38 is determined by computing per-radiation exposure event dose values for the point, and summing the per-radiation exposure event dose values for the point over the radiation exposure events. The estimating of the per-point skin dose values includes, for each radiation exposure event 30, determining whether the point 40 is an exit point 46 by determining whether an x-ray path beam from the x-ray sources 14 to the point passes inside the skin model 38. If the point 40 is determined to be an exit point 46, the per-radiation exposure event skin dose value is set to zero. To illustrate, FIG. 3 shows an illustrative beam path 42 from the x-ray source 14. This beam path 42 does not pass through the skin model 38 to reach the point 40 on the skin, but the beam path 42 does pass through the skin model 38 to reach the point 46 on the skin. Hence, the point 46 is identified as an exit point 46, and its skin dose value is therefore set to zero. (See FIG. 4 and related description for an approach for identifying exit points 46).

In other embodiments, to ensure proper placement of the skin model 38, the at least one electronic processor 20 is programmed to determine a three-dimensional position for the skin model using table coordinates retrieved from the data structure 32. The table coordinates can include a table height value of the table 15, a table thickness value of the table, and a pad thickness value of the pad 16. The table height value can be adjusted for the table thickness value and the pad thickness value to determine a height for the skin model 38. The height for the skin model 38 is positioned along a z-axis, while an x-axis and y-axis value are both set to zero.

Referring back to FIG. 2, at an operation 108, the at least one electronic processor 20 can determine whether the computed PSD estimate 36 exceeds a predetermined threshold. A notification 48 (see FIG. 1) can be output (e.g., via a visual display, and audio loudspeaker, and so forth) if the PSD estimate 36 exceeds the threshold. The notification 48 optionally includes a message suggesting that the patient should be seen by a dermatologist or otherwise examined for possible radiation-induced skin damage following the fluoroscopy procedure. It may be noted that radiation-induced skin damage is usually not immediately apparent by visual or tactile examination of the skin, but rather manifests symptoms, such as onset of skin necrosis, some hours, days, or months after the fluoroscopy procedure. A six-month check after a fluoroscopy procedure is typical. By providing the timely notification 48, early detection and treatment of radiation-induced skin damage can be achieved.

In further embodiments, the PSD estimate 36 can be used as part of a cumulative dose calculation. To do so, the at least one electronic processor 20 is programmed to retrieve multiple, previously calculated PSD estimates 36 over a course of time (for example, values within 6 month time period) from the data structure 32. A cumulative PSD estimate is calculated from these retrieved estimates. If, for example, there are two imaging procedures, where the PSD threshold for one session is "X", the PSD threshold for two imaging procedures might be, for example, 1.5X, 1.8X, 2X, etc. If this threshold is exceeded, a corresponding notification 48 can be output.

In another example, the PSD estimate 36 can be used in the cumulative dose calculation incorporating longitudinal data. For example, the PSD threshold might be adjusted, for example, lowered as the cumulative dose gets higher. Likewise, there is reporting on cumulative skin dose, so a higher PSD that might not reach the threshold for the PSD estimate 36 to output the notification 48, might be used to lower the cumulative skin dose threshold.

EXAMPLE

The calculation of the PSD estimate 36 is primarily based on the information 34 contained in an RSDR data structure 32. The RSDR data structure 32 includes information related to a geometry of exposure of the patient to an x-ray beam during the fluoroscopy procedure.

A patient position is determined for the fluoroscopy procedure using table information from the RDSR data structure 32 and a target treatment region. Any target region corresponds to one of four body regions (i.e., head, thorax, abdomen, or wholebody), and each body region has a default central coordinate. The patient position includes a lateral x-axis of the patient, a craniocaudal y-axis, and an anterior-posterior z-axis. This coordinate system is used for the skin model 38, in particular the skin model is a flattened ellipsoid in the illustrative examples. The average lateral position of the skin model 38 is determined based on the body region recorded in the DICOM, with each exposure table position determining the distance from the average. The longitudinal position and table height are taken from the RSDR data structure 32.

A position of the x-ray source(s) 14 is converted from a primary angle/alpha and a secondary angle/beta to (x,y,z) position, with the beam vector directed from this tube position to the system isocenter. The beam is shaped using the shutter position information.

A surface of the skin model 38 is defined using polar coordinates $(\theta, \varphi)$ from a center of the skin model. $\theta$ and $\varphi$ are selected such that $0 \leq \theta \leq 2\pi$ and $0 \leq \varphi \leq \pi$ (the radius is a function of the angles). The shape of the skin model 38 is a flattened ellipsoid defined by the following equations:

$$x_{skin}(\theta,\varphi) = A \cos\theta \sin\varphi$$

$$y_{skin}(\theta,\varphi) = B \cos\theta \sin\varphi$$

$$z_{skin}(\theta,\varphi) = C\sqrt{\cos\varphi} \text{ for } \cos\varphi > 0$$

$$z_{skin}(\theta,\varphi) = -C\sqrt{|\cos\varphi|} \text{ for } \cos\varphi < 0$$

A point 40 on the skin can then be given by the position vector:

$$\overrightarrow{skin} = (x_{skin}, y_{skin}, z_{skin})$$

The coefficients A, B, and C are a radius of the shape along the corresponding axis. More particularly, the coefficient A corresponds to one-half of the size of the flattened ellipsoid along the lateral x-axis direction; the coefficient B corresponds to one-half of the size of the flattened ellipsoid along the craniocaudal y-axis direction; and the coefficient C corresponds to one-half of the size of the flattened ellipsoid along the anterior-posterior z-axis direction. These coefficients are suitably chosen in order to reflect the patient size (or the size of the anatomical portion being imaged, e.g. the head) along these three mutually orthogonal directions for the position of the patient on the table 15 and the pad 16.

For a head skin model 38, the x-axis and y-axis coordinates are zero, while the z-axis is determined using the information 34 in the RSDR data structure 32. A longitudinal position of the table 14 is obtained from the RSDR data structure 32 and is used as an x-axis coordinate for the skin model 38. If such a position is missing from the RSDR data structure 32, then a default value of 0 is used so the x-ray beam is centered on a back portion of the skin model 38.

A lateral position of the table 14 is obtained from the RSDR data structure 32. This position is not in isocenter coordinates and should be converted to isocenter coordinates. To get table position in isocenter coordinates, a table offset is added to the DICOM lateral position according to:

$$TL_{DICOM} + K_{table\ offset} = P_{isocenter\ Position}$$

where K is calculated using the average lateral position from the DICOM and the target region according to:

$$K_{table\ offset} = TR_{Target\ Region\ Center} - \overline{TL_{DICOM}}$$

If such a position is missing from the RSDR data structure 32, then a default value of 0 is used so the x-ray beam is centered on a back portion of the skin model 38.

To obtain the height (i.e., z-axis) position, the table height (from the RSDR data structure 32) is subtracted by the fluoroscope height, in which the pad thickness must be accounted for. If a table height and/or system height are not available and the table height cannot be determined, a default value of (−15−PadThickness) cm should be used. If PadThickness is not provided, then that value defaults to 75 mm=7.5 cm, and the default table height value is −22.5 cm.

The dose estimate 36 at a given point 40 for a given radiation exposure event can be calculated by:

$$D = \frac{K}{R^2}$$

where R is a distance from the x-ray source 14 to the skin, and K is a dose constant for the radiation exposure (described below).

R is calculated separately for each point 40 on the patient that is within the x-ray beam during one exposure. R is a magnitude of the vector connecting a point in space where the x-ray source 14 is located, and a point 40 on the skin where the dose estimate 36 is being calculated. R is dependent on the shape of the skin model 38 used.

With particular reference to FIG. 3, to calculate R, a sum of vectors is used. A vector from a point of the position of the X-ray source 14 to an isocenter of the skin model 38, a vector from the isocenter to a patient center, and a vector from the patient center to the point 40 on the skin of the patient are summed to obtain R. The vector from the X-ray source 14 to the skin model isocenter is based on x-ray beam position. Because the isocenter is the origin of the coordinate system, this is just the opposite of the source vector with a magnitude is equal to the source-isocenter distance found in the data structure 32, but the components of the vector change with the angular position (primary and secondary angle) of the source 14. The vector from the isocenter to the patient center is based on table position and patient thickness in the z-direction, and has components related to the movement of the table 15. The vector from the patient-center to the skin point 40 is based on the equations for the flattened ellipsoid.

These vectors are summed to be equal to zero according to $$\overrightarrow{\text{source-iso}} + \overrightarrow{\text{iso-patient center}} + \overrightarrow{\text{patient center-skin}} + \overrightarrow{\text{skin-source}} = \vec{0}$$

The source-skin vector can be found by isolating the skin-source vector:

$$\overrightarrow{\text{source-iso}} + \overrightarrow{\text{iso-patient center}} + \overrightarrow{\text{patient center-skin}} =$$
$$-(\overrightarrow{\text{skin-source}}) = \overrightarrow{\text{source-skin}}$$

The value of R for a single point on the skin is the magnitude of the source-skin vector:

$$R = |\overrightarrow{\text{source-skin}}|$$

Figure 4:
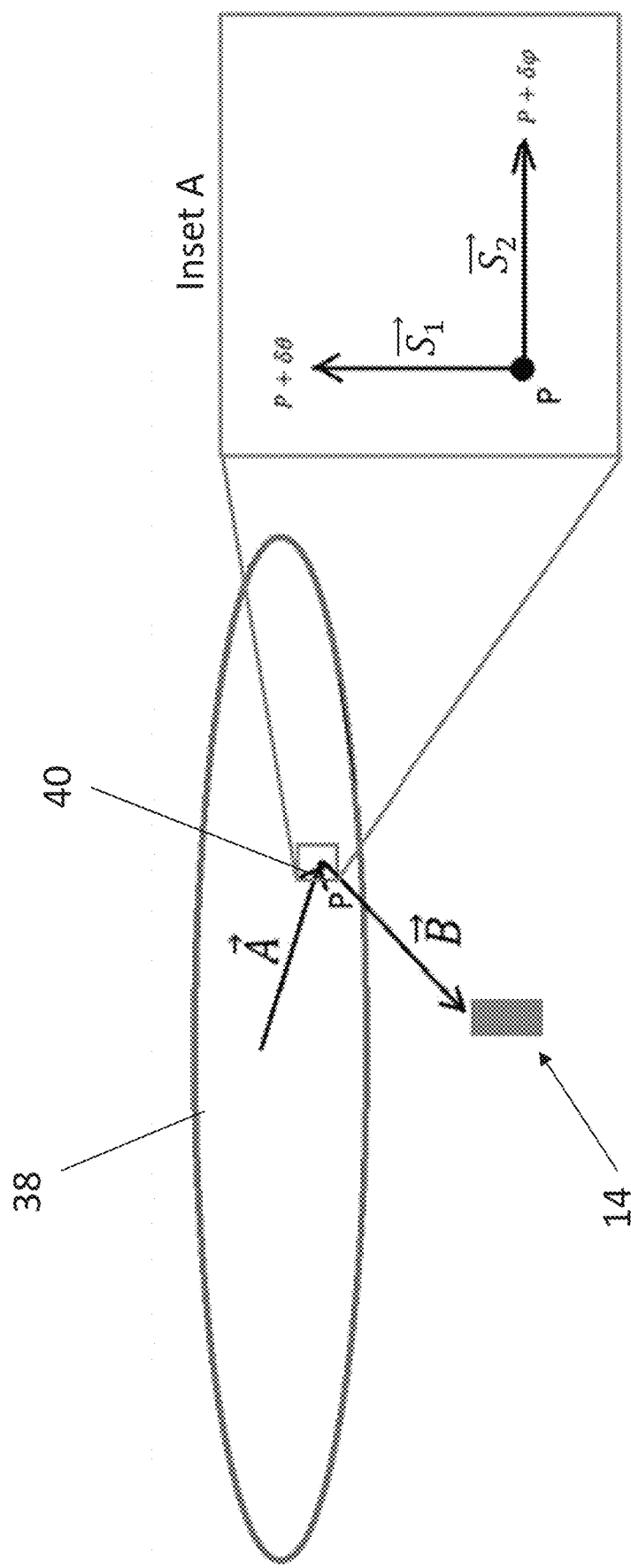
FIG. 4 diagrammatically shows an approach for determining whether a point on the skin model is an exit point.

With reference to FIG. 4, an approach for identifying whether a point is an exit point 46, i.e. a point shadowed by the body, is described. To do so, directions of vectors used to construct the geometry of the apparatus 10 can be compared. As shown in FIG. 4, a first vector $\vec{A}$ points from a center of the skin model 38 shown as an (optionally flattened) ellipsoid E(θ, φ)) to a point P 40 on the surface of the (optionally flattened) ellipsoid skin model. A second vector $\vec{B}$ points from the point P 40 to the location of the x-ray source 14. From the point P 40, as shown in FIG. 4, Inset A two small, orthogonal vectors are constructed: $\vec{S_1}$, from P to (P+δθ); and $\vec{S_2}$ from P to (P+δφ). The increments δθ and δφ are small enough that the normal of the plane formed by $\vec{S_1}$ and $\vec{S_2}$ is approximately equal to the normal of the ellipsoid skin model 38 at the P 40. The cross product of these vectors is a vector $\vec{N}$ and is orthogonal to the ellipsoid surface, though it may point either inward or outward depending on how δθ and δφ are defined.

Since the first vector $\vec{A}$ always points outward from the shape, the sign of the dot product $\vec{A} \cdot \vec{N}$ indicates which way $\vec{N}$ points: if positive, then $\vec{N}$ points outward; if negative, $\vec{N}$ points inward. The sign of the dot product $\vec{B} \cdot \vec{N}$ indicates whether $\vec{B}$ and $\vec{N}$ point in the same direction.

By comparing the signs of the vectors $\vec{A} \cdot \vec{N}$ and $\vec{B} \cdot \vec{N}$, it is determined whether the surface point P 40 is on the beam side of the ellipsoid or the opposite side (i.e., is an exit point 46). If sign($\vec{A} \cdot \vec{N}$)=sign($\vec{B} \cdot \vec{N}$), then P is on the beam side: either $\vec{N}$ points outward and points in the same direction as $\vec{B}$, or $\vec{N}$ points inward and points in the opposite direction of $\vec{B}$. If sign($\vec{A} \cdot \vec{N}$)≠sign($\vec{B} \cdot \vec{N}$) then P is an exit point 46 on the opposite side of the skin model 38.

Each event 30 has a dose constant K. Every point within the same event can use the same K value, but it should be recalculated for each event within the RDSR. K is the product of the reference point kerma, the square of the source-IRP distance, F-factor, backscatter factor, and attenuation factor according to:

$$K = \text{kerma} \cdot d_{source-IRP}^2 \cdot F \cdot B \cdot Atn$$

Kerma is a reference point dose value DoseRP, given in the data structure 32. $d_{source-IRP}$ is a distance from the x-ray source 14 to the Interventional Reference Point (IRP) (i.e., usually taken as the table height). F is an F-factor, B is a backscatter factor, and Atn is an attenuation factor.

The F factor is a function of a half-value-layer (HVL) or a kilovolt peak (KVP) value from the data structure 32. The HVL values are preferred, however the KVP values are also suitable. If neither HVL nor KVP is available, a default value of 1.5 is suitably used in some illustrative embodiments. If HVL is provided, a lookup table (e.g. such as one described in Jones, "Calculating the Peak Skin Dose resulting from Fluoroscopically Guided Interventions, Part I, Methods, November 2011, which is incorporated herein by reference) is used to determine F-factor. If HVL is exactly between two ranges, the higher value is preferably used (e.g. for 4.0, use 1.061). Input HVL should be greater than 3.0.

If KVP is used to determine F-factor, another table (disclosed in Jones) for KVP values is used. If KVP is between two ranges, the higher value is used (e.g., for 75, use 1.068).

The backscatter factor B is a function of an exposure area, which is calculated using Dose(RP) (usually Gy) and DAP (usually Gy-m$^2$) from the data structure 32. The exposure area is equal to DAP/Dose(RP), and has units of m$^2$. This should be converted to cm$^2$ to determine backscatter factor B. The backscatter factor is dependent on whether the exposure area is greater or less than 225 cm$^2$. If no DAP is available, the default backscatter factor 1.5 is used, and can also use a corresponding look-up table described in Jones.

The attenuation factor Atn is applied depending on whether or not the beam is passing through the table 15 and pad 16 in order to reach the patient (as is the case, for example, for the beam path B shown in FIG. 3). If table height is greater than the source height (z-coordinate), then the beam is shining through table. When the beam is passing through the table, a projection factor Pj is calculated. The projection factor Pj is the inverse of the dot product of the unit vector along the source coordinate and the vector (0, 0, −1) according to:

$$Pj = \left( \frac{\overrightarrow{source}}{\|\overrightarrow{source}\|} \cdot (0, 0, -1) \right)^{-1}$$

The effective thickness of the pad and table are given by:

$$x_{table,eff} = x_{table} * Pj$$

$$x_{pad,eff} = x_{pad} * Pj$$

where $x_{table}$ (i.e., default 3.5 cm) is the table thickness and $x_{pad}$ (i.e., default 7.5 cm) is the pad thickness.

Attenuation by the effective thicknesses of the pad and table are multiplied, then normalized to the attenuation due to the unadjusted thickness of the table:

$$Atn = \frac{\exp(-\mu_{pad} x_{pad,eff}) \cdot \exp(-\mu_{table} x_{table,eff})}{\exp(-\mu_{table} x_{table})}$$

where $\mu_{pad}$ is the attenuation coefficient of the pad, which may be provided by the user. Default value is 0.05 cm$^{-1}$ and $\mu_{table}$ is the attenuation coefficient of the table, which may be provided by the user. Default value is 0.028 cm$^{-1}$. If the beam is not found to be projecting through the table, then the attenuation factor is found by:

$$Atn = \frac{1}{\exp(-\mu_{table} x_{table})}$$

In a clinical environment, RDSR files (or, alternatively, another DICOM data structure 32 used to store the information 34 for the radiation exposure events) may or may not have all information used in estimating the PSD. This can depend on the vendor of the fluoroscope 12, the software version deployed in running the fluoroscope 12, private tags availability, and whether (and the extent by which) the RDSR is populated by the Radiology Information System (RIS). In the event private tags and other tags useful in calculating the peak skin dose are not available in the RDSR, then default values will be used to the extent that a more accurate skin dose estimate can be generated than simply using the cumulative air kerma value to estimate skin dose. If the available data do not support a more accurate estimate of skin dose (that is, calculation of the PSD), then the cumulative air kerma value only will be provided in the summary report and the peak skin dose (PSD) field will be null.

The table below presents the patient, system and event level data elements that are used to generate an estimate of the peak skin dose. Note that the class of parameters identified as Event Data are stored for each radiation exposure event. When the actual value cannot be extracted from the RSDR, then the corresponding default value will be used. Some values are intended to be provided by the user if fluoroscopy machines are to be connected, and peak skin dose estimates are to be provided. For example, the user can enter the pad and table thickness and attenuation values that are measured by the facility's medical physicist, and input for each machine into the configuration file during installation. If the configuration fields are not completed at installation or any time thereafter, the default values will be used. (Data elements in BOLD indicate that a value must be present for any estimate of peak skin dose to be calculated. These include only the Fluoroscopy AK and Acquisition AK for each radiation exposure event.)

| Class | Data Element | Symbol | Data Type (F-Fixed, V-Variable) | How obtained (DICOM Tag #) | Default |
|---|---|---|---|---|---|
| Patient Data | Patient Name | PN | F | | — |
| | Patient ID | PID | F | | — |
| | Patient height -torso | PHT | F | Config setting | 88 cm |
| | Patient width - torso | PWT | F | Config setting | 30 cm |
| | Patient thickness - torso | PTK | F | Config setting | 20 cm |
| | Patient circumference - head | PCF | F | Config setting | 16 cm |
| | Date of procedure | DOP | F | | — |
| | Procedure | PC | F | | — |
| | Performing Physician | PP | F | | — |
| System Data | Table offset | TO | F | | 0, 0 |
| | Source to isocenter | SIC | F | | 810 mm |
| | Interv. Ref. Pt. Definition | IRP | F | | 0, 0, −15 cm |
| | Pad thickness | PTK | F | Config setting | 75 mm |
| | Table thickness | TTK | F | Config setting | 50 mm |
| | Pad attenuation | PAT | F | Config setting | 0.05/cm |
| | Table attenuation | TAT | F | Config setting | 0.028/cm |
| | F-factor | F | F | Config setting | 1.07 |
| | Backscatter factor | B | F | Config setting | 1.5 |
| Event Data | Table height | THT | V | | IRP |
| | Table lat. Position | TLaP | V | | 0 |
| | Table long. Position | TLoP | V | | 0 |
| | Body Region | BR | V | | Whole Body |
| | System height | SHT | V | | ? |
| | Beam prim. Angle | BPA | V | | 0 |
| | Beam sec. angle | BSA | V | | 0 |
| | Shutter position | SHP | V | | 157.5, 121.5 mm |
| | Source - image dis. | SID | V | | 900 mm |
| | Acquisition DAP | ADAP | V | | — |
| | Acquisition AK | AKA | V | | — |
| | Fluoroscopy DAP | FDAP | V | | — |
| | Fluoroscopy AK | FAK | V | | — |
| | Acquisition time | AT | V | | — |

-continued

| Class | Data Element | Symbol | Data Type (F-Fixed, V-Variable) | How obtained (DICOM Tag #) | Default |
|---|---|---|---|---|---|
| | Fluoroscopy time | FT | V | | — |
| | Rotational acquisition DAP | RAQ | V | | — |
| Procedure Data | Cum. Acquisition AK | CAAK | F | | |
| | Cum. Acquisition DAP | CADAP | F | | |
| | Cum Fluoroscopy AK | CFAK | F | | |
| | Cum Fluoroscopy DAP | CFDAP | F | | |
| | Total Cumulative AK | TCAK | F | | |
| | Total Cumulative DAP | CDAP | F | | — |
| | Total Peak Skin Dose | PSD | F | Calculated | — |

Default values are chosen to allow the program to function even when nonessential data are missing from the procedure report. The design parameters were such that choosing a conservative value (higher dose) was preferable to underestimating the dose to the patient. Units for the table were chosen based on typical values used in the RSDR. When determining table height default position, it is standard to assume that the skin is at the IRP. Since System Height and Table offset are used to calculate table position, they do not have default values. Instead when their values are missing the default table positions are used. The "Reference point definition" field contains a string noting the definition of the reference point. The value "15 cm below isocenter" is commonly present. IRP is defaulted to 15 centimeters below isocenter because this is standard. The Table Lateral and Table Longitudinal positions are defaulted to zero, which places exposures on the center of the phantom. This minimizes geometrical effects and maximizes exposure overlap to provide a conservative estimate of PSD. The primary and secondary angle defaults are chosen to be 0 degrees. This is standard when estimating doses manually. It causes all the doses to overlap, providing a conservative estimate of PSD. The Shutter position defaulted to being fully open to provide a conservative value of 900 mm. The Pad and Table attenuation values are based on ion chamber measurements. These coefficients are used to calculate the attenuated kerma value K according to $K = K_0^{(-\mu x)}$, where $K_0$ is the unattenuated kerma, x is the thickness of the pad or table, and $\mu$ is the appropriate attenuation coefficient. The F-Factor is suitably given in Table 1 or Table 2, and the Back Scatter Factor (B) from Table 3. These values were derived from literature [see Jones, et al. Calculating the peak skin dose resulting from fluoroscopically guided interventions. Part I: Methods, JACMP 12:4, Fall 2011]. F-Factor is the ratio of the energy attenuation coefficient ($\mu\_en/\rho$) of the detection medium to that of air, and ranges from 1.058 to 1.07 depending on beam quality. BSF theoretically ranges from 1.2 to 1.6, but practically ranges between 1.35 and 1.5. Defaults were chosen to be conservative. HVL and DAP are used to estimate BSF, so if either is not available then a default BSF is used.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. An apparatus, comprising:
at least one electronic processor programmed to:
   control an X-ray imaging device to perform an X-ray imaging procedure on a patient, wherein the X-ray imaging procedure comprises a plurality of radiation exposure events;
   automatically construct a data structure which stores information for the radiation exposure events, including at least radiation dose information for the radiation exposure events determined during the X-ray imaging procedure;
   compute a peak skin dose (PSD) estimate for the X-ray imaging procedure from the information for the radiation exposure events retrieved from the data structure, wherein, to compute the PSD estimate, the at least one electronic processor is programmed to:
      estimate a per-point skin dose value for points on a skin model representing the patient from the information for the radiation exposure events, and
      compute the PSD estimate as the estimated per-point skin dose value having a highest value;
   determine whether the PSD estimate exceeds a PSD threshold; and
   output a notification if the PSD estimate exceeds the PSD threshold.

2. The apparatus of claim 1, wherein the at least one electronic processor is further programmed to:
   determine the radiation dose information for the radiation exposure events based on settings of the X-ray imaging device during the radiation exposure events and X-ray imaging times and acquisition times of the radiation exposure events.

3. The apparatus of claim 1, wherein the skin model comprises a flattened ellipsoid calculated from polar coordinates from a center of the flattened ellipsoid and a radius of a shape along each of a corresponding x-axis, y-axis, and z-axis of the flattened ellipsoid.

4. The apparatus of claim 3, wherein the at least one electronic processor is programmed to:
   determine a three-dimensional position for the skin model using table coordinates retrieved from the data structure.

5. The apparatus of claim 4, wherein, to determine the three-dimensional position for the skin model, the at least one electronic processor is further programmed to:
   retrieve a table height value from the data structure;
   retrieve a table thickness value from the data structure;
   retrieve a pad thickness value from the data structure; and adjust the table height value for the table thickness value and the pad thickness value to determine a height for the skin model.

6. The apparatus of claim 1, wherein the skin model comprises a flattened ellipsoid in which the points on the skin model have coordinates:

$$\overrightarrow{skin} = (x_{skin}, y_{skin}, z_{skin})$$

where:

$$x_{skin}(\theta, \varphi) = A\cos\theta\sin\varphi$$

$$y_{skin}(\theta, \varphi) = B\sin\theta\sin\varphi$$

$$z_{skin}(\theta, \varphi) = C\sqrt{\cos\varphi} \text{ for } \cos\varphi > 0$$

$$z_{skin}(\theta, \varphi) = -C\sqrt{|\cos\varphi|} \text{ for } \cos\varphi < 0.$$

7. The apparatus of claim 1, wherein, to determine the per-point skin dose value for each point on the skin model, the at least one electronic processor is further programmed to:
compute per-radiation exposure event skin dose values for the point on the skin model and sum the per-radiation exposure event skin dose values for the point over the radiation exposure events,
wherein the computation of the per-radiation exposure event skin dose values for the point on the skin model includes, for each radiation exposure event:
determining whether the point is an exit point by determining whether an X-ray path beam from an X-ray source to the point passes inside the skin model, and
setting the per-radiation exposure event skin dose values to zero if the point is an exit point.

8. The apparatus of claim 1, wherein the PSD estimate for the X-ray imaging procedure is computed using only the information for the radiation exposure events retrieved from the data structure.

9. The apparatus of claim 1, wherein the at least one electronic processor is programmed to:
retrieve multiple, previously-calculated PSD estimates from the data structure; and
calculate a cumulative PSD estimate from the multiple previously-calculated PSD estimates.

10. The apparatus of any claim 1, wherein the at least one electronic processor is programmed to:
retrieve multiple, previously-calculated PSD estimates from the data structure; and
adjust the PSD threshold based on the multiple previously-calculated PSD estimates.

11. The apparatus of claim 1, wherein the notification is indicative of whether a patient should seek medical attention following the X-ray imaging procedure.

12. A non-transitory computer readable medium storing instructions, which, when executed by a processor, cause the processor to:
control an imaging device to perform an imaging procedure on a patient, wherein the imaging procedure comprises a plurality of radiation exposure events;
construct a data structure which stores information for the radiation exposure events, including at least radiation dose information for the radiation exposure events determined during the imaging procedure;
estimate a per-point skin dose value for points on a skin model representing the patient from the information for the radiation exposure events retrieved from the data structure;
compute a PSD estimate as the estimated per-point skin dose value having a largest value;
determine whether the PSD estimate exceeds a PSD threshold; and
output a notification if the PSD estimate exceeds the PSD threshold.

13. The non-transitory computer readable medium of claim 12, wherein the skin model comprises a flattened ellipsoid in which the points on the skin model have coordinates:

$$\overrightarrow{skin} = (x_{skin}, y_{skin}, z_{skin})$$

where:

$$x_{skin}(\theta, \varphi) = A\cos\theta\sin\varphi$$

$$y_{skin}(\theta, \varphi) = B\sin\theta\sin\varphi$$

$$z_{skin}(\theta, \varphi) = C\sqrt{\cos\varphi} \text{ for } \cos\varphi > 0$$

$$z_{skin}(\theta, \varphi) = -C\sqrt{|\cos\varphi|} \text{ for } \cos\varphi < 0.$$

14. The non-transitory computer readable medium of claim 12, wherein the instructions, when executed by the processor, further cause the processor to:
determine a three-dimensional position for the skin model using table coordinates retrieved from the data structure.

15. The non-transitory computer readable medium of claim 14, wherein to determine the three-dimensional position for the skin model, the instructions, when executed by the processor, further cause the processor to:
retrieve a table height value from a data structure;
retrieve a table thickness value from the data structure;
retrieve a pad thickness value from the data structure; and
adjust the table height value for the table thickness value and the pad thickness value to determine a height for the skin model.

16. The non-transitory computer readable medium of claim 12, wherein the skin model comprising a flattened ellipsoid calculated from polar coordinates from a center of the flattened ellipsoid and a radius of a shape along each of a corresponding x-axis, y-axis, and z-axis of the flattened ellipsoid.

17. A peak skin dose (PSD) computation method, comprising:
controlling a fluoroscope to perform a fluoroscopy procedure on a patient, wherein the fluoroscopy procedure comprises a plurality of radiation exposure events;
automatically constructing a data structure which stores information for the radiation exposure events, including at least radiation dose information for the radiation exposure events determined during the fluoroscopy procedure;
estimating a per-point skin dose value for points on a skin model representing the patient from the information for the radiation exposure events retrieved from the data structure;
computing the PSD estimate as the estimated per-point skin dose value having a largest value;
determining whether the PSD estimate exceeds a PSD threshold; and
outputting a notification if the PSD estimate exceeds the PSD threshold.

18. The method of claim 17, further comprising:
constructing the skin model as a flattened ellipsoid calculated from polar coordinates from a center of the flattened ellipsoid and a radius of a shape along each of a corresponding x-axis, y-axis, and z-axis of the flattened ellipsoid.

19. The method of claim 17, wherein: the estimating of the per-point skin dose value further comprises:
determining the per-point skin dose value for each point on the skin model by computing per-radiation exposure event dose values for the point and summing the per-radiation exposure event dose values for the point over the radiation exposure events; and
for each radiation exposure event:
determining whether the point is an exit point by determining whether an x-ray path beam from an x-ray source to the point passes inside the skin model,
setting the per-radiation exposure event skin dose value to zero if the point is located away from an x-ray source of the fluoroscope, and
setting the per-radiation exposure event skin dose value to zero if the point is an exit point.

20. The method of claim 17, further comprising:
determining a three-dimensional position for the skin model using table coordinates retrieved from the data structure by:
retrieving a table height value, a table thickness value, and a pad thickness value from the data structure, and
adjusting the table height value for the table thickness value and the pad thickness value to determine a height for the skin model; and
computing the PSD estimate based on the three-dimensional position for the skin model.

* * * * *